(12) United States Patent
Kim et al.

(10) Patent No.: US 10,996,181 B2
(45) Date of Patent: May 4, 2021

(54) SENSOR

(71) Applicant: LG ELECTRONICS INC., Seoul (KR)

(72) Inventors: Hyunchul Kim, Seoul (KR); Myungwon Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 67 days.

(21) Appl. No.: 16/473,212

(22) PCT Filed: Dec. 20, 2017

(86) PCT No.: PCT/KR2017/015121
§ 371 (c)(1),
(2) Date: Jun. 24, 2019

(87) PCT Pub. No.: WO2018/131818
PCT Pub. Date: Jul. 19, 2018

(65) Prior Publication Data

US 2019/0331623 A1 Oct. 31, 2019

Related U.S. Application Data

(60) Provisional application No. 62/445,206, filed on Jan. 11, 2017.

(30) Foreign Application Priority Data

Nov. 20, 2017 (KR) .................. 10-2017-0154814

(51) Int. Cl.
*G01N 27/12* (2006.01)
*B41F 13/11* (2006.01)
(Continued)

(52) U.S. Cl.
CPC .............. *G01N 27/12* (2013.01); *B41F 13/11* (2013.01); *B41F 15/06* (2013.01); *H01Q 1/22* (2013.01);
(Continued)

(58) Field of Classification Search
None
See application file for complete search history.

(56) References Cited

U.S. PATENT DOCUMENTS 5,185,256 A * 2/1993 Nankai .................. C12Q 1/004
435/174
6,746,584 B1 * 6/2004 Wang ................... G01N 27/419
204/406
(Continued)

FOREIGN PATENT DOCUMENTS

KR 10-2007-0102858 A 10/2007
KR 10-2015-0011179 A 1/2015
(Continued)

OTHER PUBLICATIONS

Escobedo et al., "Flexible Passive Near Field Communication Tag for Multigas Sensing," Analytical Chemistry, vol. 89, No. 3, 2017 (Published Dec. 24, 2016), pp. 1697-1703, XP055632629.
(Continued)

*Primary Examiner* — Jas A Sanghera
(74) *Attorney, Agent, or Firm* — Birch, Stewart, Kolasch & Birch, LLP (57) ABSTRACT

Provided is a sensor comprising a non-conductive substrate; and a conductive layer electronically printed on one side of the substrate, wherein the conductive layer comprises: an antenna pattern for transmitting and receiving a radio signal with an external device; a sensing electrode connected to the antenna pattern via a circular wiring for sensing an impedance change due to contact with a sensing target material; and a coating electrode stacked on the sensing electrode for removing an occurrence of noise of the impedance change. Accordingly, the present invention solves the problem of a sensor, in the form of a terminal, not being compact and the problem of high manufacturing costs and low manufacturing quality of a sensor manufactured using a deposition method in order to replace such sensor with a sensor manufactured by a printing method, and solves a corrosion problem of a (Continued)

sensing electrode, a durability problem, etc. that may occur in the sensor of the printing method.

19 Claims, 9 Drawing Sheets

(51) Int. Cl.
    *B41F 15/06*     (2006.01)
    *H01Q 1/22*     (2006.01)
    *H01Q 1/36*     (2006.01)
    *H01Q 1/38*     (2006.01)
    *G01N 33/03*     (2006.01)

(52) U.S. Cl.
    CPC .............. *H01Q 1/368* (2013.01); *H01Q 1/38* (2013.01); *G01N 33/03* (2013.01)

(56) References Cited

U.S. PATENT DOCUMENTS

| | | | | |
|---|---|---|---|---|
| 2001/0030545 A1* | 10/2001 | Schmitt | ................ | G01N 27/223 |
| | | | | 324/664 |
| 2003/0188427 A1* | 10/2003 | Say | ........................ | G01N 33/66 |
| | | | | 29/846 |
| 2006/0131171 A1* | 6/2006 | Kobayashi | ........ | B01L 3/502707 |
| | | | | 204/403.01 |
| 2011/0011179 A1* | 1/2011 | Gustafsson | .......... | G01N 27/223 |
| | | | | 73/335.03 |
| 2013/0230429 A1 | 9/2013 | Naishadham et al. | | |
| 2015/0077296 A1* | 3/2015 | An | ........................ | H01Q 1/2225 |
| | | | | 343/720 |
| 2016/0161434 A1 | 6/2016 | Yan et al. | | |

FOREIGN PATENT DOCUMENTS

| KR | 10-2015-0080224 A | 7/2015 |
|---|---|---|
| KR | 10-2016-0015370 A | 2/2016 |
| KR | 10-2016-0132750 A | 11/2016 |

OTHER PUBLICATIONS

Kutty et al., "A Novel Carbon Nanotube Loaded Passive UHF RFID Sensor Tag with Built-in Reference for Wireless Gas Sensing," 2016 IEEE MTT-S International Microwave Symposium (IMS), 2016 (May 22, 2016), 4 pages, XP032941352.

Quintero et al., "Smart RFID Label with a Printed Multisensor Platform for Environmental Monitoring," Flexible and Printed Electronics, vol. 1, No. 2, 2016 (Published May 17, 2016), pp. 1-12 (total 13 pages), XP055417565.

\* cited by examiner

SENSOR

CROSS REFERENCE TO RELATED APPLICATIONS

This application is the National Phase of PCT International Application No. PCT/KR2017/015121, filed on Dec. 20, 2017, which claims priority under 35 U.S.C. 119(e) to U.S. Provisional Application No. 62/445,206, filed on Jan. 11, 2017 and under 35 U.S.C. 119(a) to Patent Application No. 10-2017-0154814, filed in Republic of Korea on Nov. 20, 2017, all of which are hereby expressly incorporated by reference into the present application.

TECHNICAL FIELD

The present invention relates to a printing type sensor that senses an impedance change of a target material to measure salinity and a sugar content and determine a denaturalization level of edible oil and fat and transmits the sensed result to simply check the sensed result.

BACKGROUND ART

Generally, a sensor of the related art is provided in the form of a terminal to measure salinity and a sugar content and determine a denaturalization level of edible oil and fat.

A terminal type sensor has advantages in that measurement and output of a measured result may be performed without a separate device, but should be provided with a separate power supply, whereby a problem occurs in that volume, weight, etc. are increased.

Particularly, with the trend of increasing users who necessarily use a mobile terminal such as a smartphone, it is considered to replace some functions of a sensor with those of a power supply unit and an output unit of a smartphone.

Therefore, a portable sensor is required, which performs only a measurement function of a material and transmits the measured result to an external device or receives a sensing signal.

However, for such a portable sensor, it is necessary to consider a material and structure for obtaining an exact measured value while satisfying a small size.

In a portable sensor for implementing the material and structure, it is general that a vacuum deposition method is used to form a conductive area such as a sensing electrode. The vacuum deposition method may cause deformation of a substrate due to a process condition of a high temperature and cause increase of the manufacturing cost.

Therefore, a sensor manufactured by a printing method may be considered to substitute for the vacuum deposition method. Moreover, it is required to solve a corrosion problem and a reliability problem such as durability degradation, which may occur in the sensor of the printing method.

DISCLOSURE

Technical Problem

An object of the present invention is to solve the aforementioned problems of a sensor, in the form of a terminal, not being compact and the problem of high manufacturing costs and low manufacturing quality of a sensor manufactured using a deposition method in order to replace such a sensor with a sensor manufactured by a printing method, Another object of the present invention is to provide a sensor by solving a corrosion problem of a sensing electrode, a durability problem, etc. that may occur in a sensor of a printing method.

Technical Solution

According to one aspect of the present invention to achieve the above problems or other problems, there is provided a sensor comprising a non-conductive substrate; and a conductive layer electronically printed on one surface of the substrate, wherein the conductive layer includes an antenna pattern for transmitting or receiving a radio signal to or from an external device; a sensing electrode connected to the antenna pattern through a circuit line, for sensing an impedance change due to a contact with a sensing target material; and a coating electrode deposited on the sensing electrode, for removing an occurrence of noise of the impedance change.

Also, according to another aspect of the present invention, there is provided a sensor characterized in that each of the sensing electrode and the coating electrode includes a plurality of conductive particles forming a gap, and a binder having the plurality of conductive particles to fill the gap.

Also, according to another aspect of the present invention, there is provided a sensor characterized in that the conductive particles of the sensing electrode include Ag.

Also, according to another aspect of the present invention, there is provided a sensor characterized in that the conductive particles of the coating electrode include a carbon nano tube (CNT).

Also, according to another aspect of the present invention, there is provided a sensor characterized in that the conductive particles of the coating electrode further include a Graphite and a carbon black.

Also, according to another aspect of the present invention, there is provided a sensor characterized in that the graphite and the carbon black are configured at 10% or less of a total mass of the coating electrode.

Also, according to another aspect of the present invention, there is provided a sensor characterized in that the binder includes one of a Polyethylene oxide (PEO) based resin, an Oleic acid based resin, an Acrylate based resin, an Acetate based resin, and an Epoxy based resin.

Also, according to another aspect of the present invention, there is provided a sensor characterized in that the conductive particles are configured by combination of a flake shape or a spherical shape.

Also, according to another aspect of the present invention, there is provided a sensor characterized in that the antenna pattern, the circuit line and the sensing electrode are made of the same material, provided on the same layer, and the coating electrode is provided by being deposited on the sensing electrode.

Also, according to another aspect of the present invention, there is provided a sensor characterized in that the sensing electrode includes two electrodes spaced apart from each other, the coating electrode includes a first area and a second area, which respectively cover the spaced electrodes, and a minimum distance between the first area and the second area is 10 μm, and a thickness of the coating electrode from an upper end of the sensing electrode is 10 μm.

Also, according to another aspect of the present invention, there is provided a sensor characterized in that the sensing electrode includes two electrodes spaced apart from each other, and an interval between the two electrodes is 30 μm or more and 3000 μm or less.

Also, according to another aspect of the present invention, there is provided a sensor characterized in that the antenna pattern, the sensing electrode and the circuit line have a thickness of 0.5 μm or more and 15 μm or less.

Also, according to another aspect of the present invention, there is provided a sensor characterized in that the substrate includes any one of polyethylene erephthalate (PET), polyimide (PI), polystyrene (PS) and polyethylene naphthalate (PEN).

Also, according to another aspect of the present invention, there is provided a sensor characterized in that the antenna pattern has a width of 500 μm or more and 1500 μm or less, and an adjacent distance of the antenna pattern is 300 μm or more and 700 μm or less.

Also, according to another aspect of the present invention, there is provided a sensor further comprising a passivation layer forming an opening, which exposes at least one area of the sensing electrode, having a surface energy greater than that of the substrate.

Also, according to another aspect of the present invention, there is provided a sensor further comprising a protective layer deposited on the substrate, protecting the conductive layer and the passivation layer.

Also, according to still another aspect of the present invention, there is provided a sensor comprising a non-conductive substrate; and a conductive layer electronically printed on one surface of the substrate, wherein the conductive layer includes an antenna pattern for transmitting or receiving a radio signal to or from an external device, a sensing electrode connected to the antenna pattern through a circuit line, for sensing an impedance change due to a contact with a sensing target material, and a conjugate polymer layer containing a conductive polymer provided by being patterned or absorbed in the sensing electrode.

Also, according to further still another aspect of the present invention, there is provided a sensor comprising a non-conductive substrate, and a conductive layer electronically printed on one surface of the substrate, wherein the conductive layer includes an antenna pattern for transmitting or receiving a radio signal to or from an external device, and a sensing electrode connected to the antenna pattern through a circuit line, for sensing an impedance change due to a contact with a sensing target material, and the sensing electrode is pressed through a rolling process.

Advantageous Effects of the Invention

Advantageous effects of a sensor according to the present invention are as follows.

According to at least one of the embodiments of the present invention, a compact sensor linked to an external device may be provided.

According to at least one of the embodiments of the present invention, a sensor is capable of being manufactured at a low temperature to reduce the probability of occurrence of a defect rate caused by deformation.

According to at least one of the embodiments of the present invention, a sensor is capable of being manufactured by minimum layers for several conductive components to reduce the manufacturing cost.

According to at least one of the embodiments of the present invention, a sensor is capable of being manufactured at a low cost through an electronic printing method.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

FIGS. 9($a$) and 9($b$) are graphs illustrating that an ADC change according to measurement times for each of a sensor of the related art and a sensor of the present invention is measured.

BEST MODE FOR CARRYING OUT THE INVENTION

Figure 1:
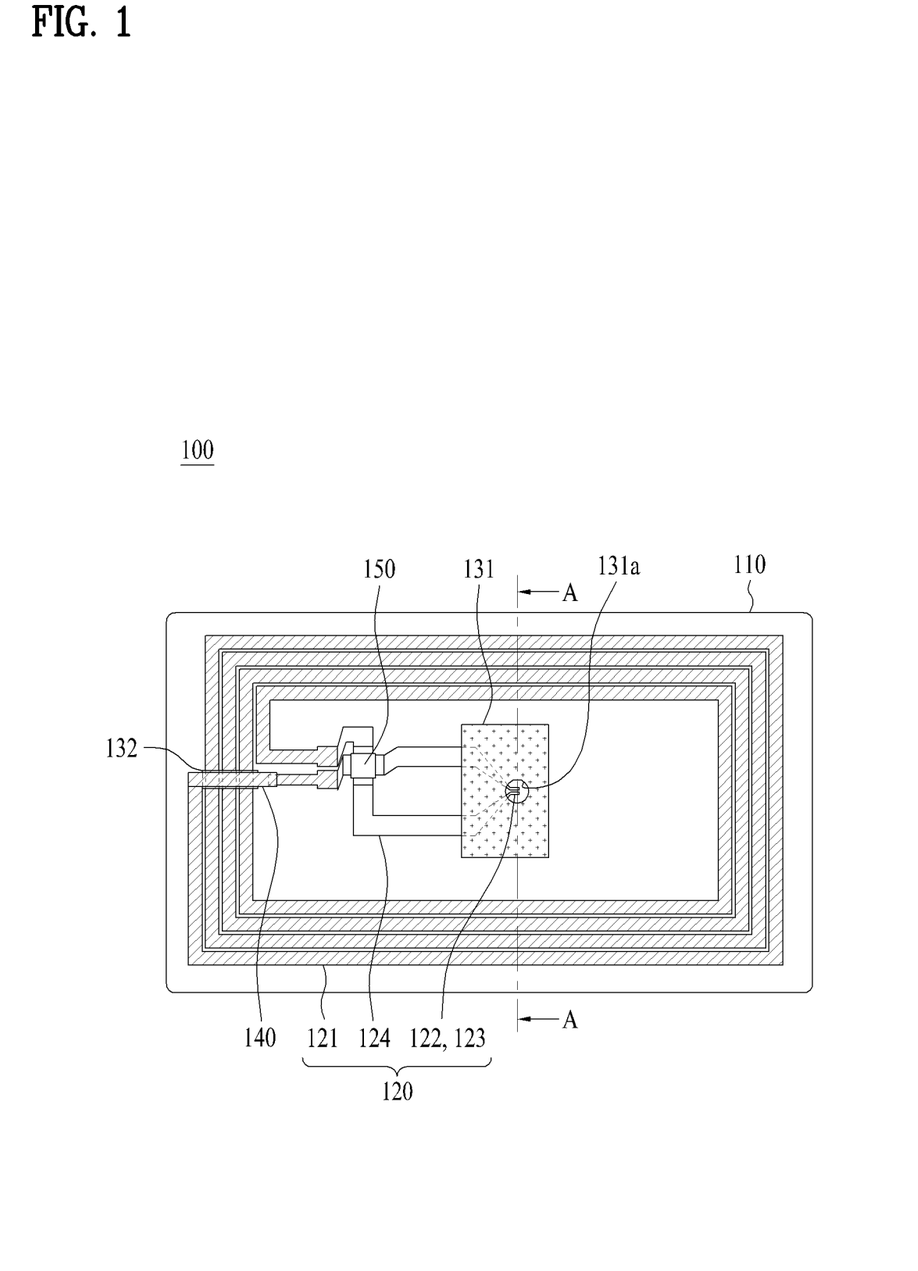
FIG. 1 is a front view illustrating a sensor according to one embodiment of the present invention.
Figure 2:
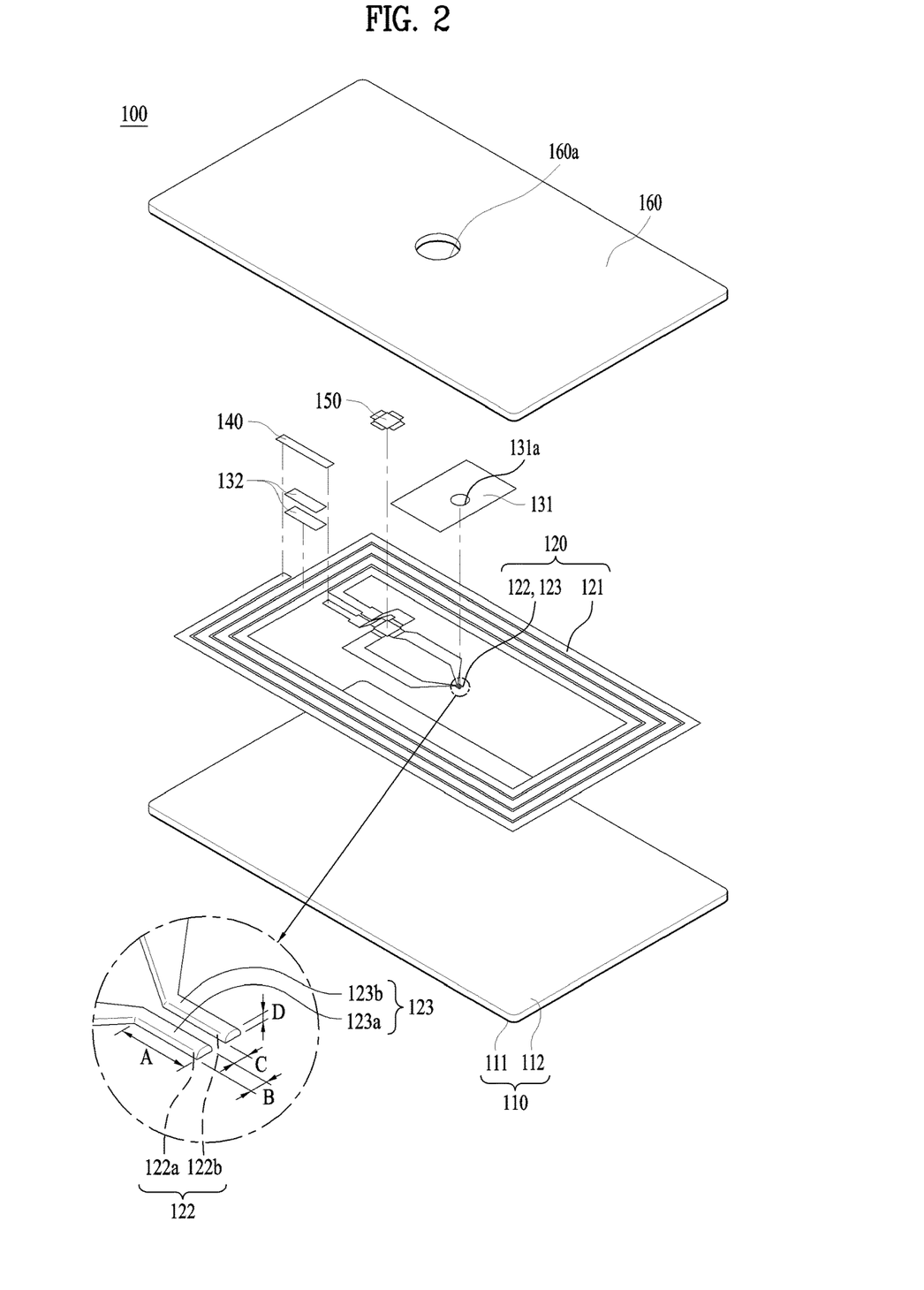
FIG. 2 is an exploded perspective view illustrating a sensor of FIG. 1.

FIG. 1 is a front view illustrating a sensor 100 according to one embodiment of the present invention, and FIG. 2 is an exploded perspective view illustrating a sensor 100 of FIG. 1. For convenience of description, description will be given with reference to FIGS. 1 and 2 together.

The sensor may comprise a substrate 110, a conductive layer 120, and an insulating layer. In this case, the conductive layer 120 may include an antenna pattern 121, a sensing electrode 122, and a circuit line 124.

The substrate 110 configures a non-conductive layer. The substrate 110 serves as a target in which the conductive layer 120 is packaged. For example, the substrate 110 may include a plastic layer 111 and a silica layer 112.

The plastic layer 111 is made of plastic (polymer compound or synthetic resin) having flexibility. The plastic may include at least one selected from a group of a polyethylene erephthalate (PET), a polyimide (PI), a polystyrene (PS) and a polyethylene naphthalate (PEN).

The silica layer 112 may be coated on one surface of the plastic layer 111. The silica layer 112 may be formed between the plastic layer 111 and the conductive layer 120. The silica layer 112 enables fast diffusion of a sensing target material 10, especially solution, stability of the sensing target material 10, and attachment intensity enhancement of the conductive layer 120. The silica layer 112 may have a thickness of several nm to several tens of nm.

The conductive layer 120 may be provided on one surface of the substrate 110.

The conductive layer 120 may include an antenna pattern 121, a circuit line 124 and a sensing electrode, as described above.

The sensing electrode 122 causes an impedance change by a contact of the sensing target material 10. The impedance change may mean a state of the sensing target material 10.

Details of the sensing electrode 122 will be described later.

The antenna pattern 121 transmits or receives a radio signal to or from an external device. For example, the antenna pattern 121 may serve to receive a sensing command signal of the external device to measure an impedance change of the sensing target material 10 or transmit the measured impedance change value to the external device.

The circuit line 124 forms a passage for signal transfer by electrically connecting the antenna pattern 121 with the sensing electrode 122.

The conductive layer 120 may be formed in a single body. The case that the antenna pattern 121, the sensing electrode 122 and the circuit line 124 of the conductive layer 120 are formed in a single body may mean that they are functionally identified from one another but may structurally be formed of the same material by the same process in view of the manufacturing process. However, as the case may be, the coating electrode 123 of the conductive layer 120 may be formed of a hetero-material unlike the other components or implemented by a process different from that of the other components. A detailed description of the coating electrode will be described later.

Alternatively, if necessary, the components of the conductive layer 120 may be formed respectively by a separate process without being formed in a single body.

The conductive layer 120 provided in a single body may not be detachable physically.

The conductive layer 120 may be formed on the substrate 110 by an electron printing method.

The conductive layer 120 of the related art is formed by a vacuum deposition method. The conductive layer 120 formed by the vacuum deposition method is advantageous in that it has a stable structure but the manufacturing and material costs are increased in that addition process such as etching is required after vacuum deposition, and a shape deformation of the substrate 110 may be caused by the process performed at a high temperature.

The electronic printing process of the conductive layer 120 may be performed by any one method of Gravure offset, Gravure printing, and Screen printing.

At least some of the conductive layer 120 may be formed as the same layers. The case that at least some of the conductive layer 120 are formed of the same material as the same layers may mean that the conductive layer 120 is printed on the substrate 110 by a printing process of one time in view of the manufacturing process. If the conductive layer 120 is printed by a printing process of one time, the manufacturing process may be simplified, whereby the manufacturing cost and time may be minimized.

In detail, an area of the conductive layer 120 formed as the same layer may include all or some of the antenna pattern 121, and the circuit line 124 and the sensing electrode 122. A detailed description of the conductive layer 120 will be given later.

The antenna pattern 121 transmits or receives a signal to or from an external device.

The external device may mean an electronic device having a communication function. For example, examples of the external device include a smartphone, a computer, a digital broadcasting terminal, a PDA, etc.

The antenna pattern 121 generates a direct current power source by receiving a radio signal from the external device, wherein the generated direct current power source is used for measurement driving of the sensor 100. A measured impedance difference of the sensing target material 10 may again be transmitted to the external device through the antenna pattern 121.

Since the direct current power source is generated by the antenna pattern 121, the sensor 100 may not be provided with a separate power supply unit. This may result in a compact size of the sensor 100 and minimize the manufacturing cost.

The antenna pattern 121 may be formed on one surface of the substrate 110 two-dimensionally. Particularly, the antenna pattern 121 may be provided along outer corners of the substrate 110 to make sure of an antenna length, and may be provided in a screw shape by being wound several times in accordance with a necessary length. A shape and pattern of the antenna pattern 121 may be change in various ways to implement an antenna function.

The antenna pattern 121 may have a line width of 500 µm to 1500 µm to have high inductance. An interval of the antenna pattern 121, which is wound several times, with an adjacent line may be of 300 µm to 700 µm to make sure of an appropriate capacitance component.

The antenna pattern 121 may include a pattern area for performing an original function of an antenna, and a connection area for electrically connecting the pattern area with the circuit line 124 or the sensing electrode 122. The pattern area and the connection area may be provided on the same layer, but may be provided on their respective layers different from each other to actively perform electrical connection with the other components. To this end, an insulating area may additionally be provided to avoid an unintended electrical connection between different layers. A detailed description of the insulating area will be given later.

The antenna pattern 121 may operate as a radiator of an NFC (Near Field Communication) antenna. Information exchange of the NFC antenna may be performed using communication options of 13.56 MHz.

The circuit line 124 electrically connects the antenna pattern 121 with the sensing electrode 122. Also, the circuit line 124 may electrically be connected with a device 150 for controlling the sensor 100. That is, the circuit line 124 may mean all areas except the antenna pattern 121 and the sensing electrode 122 of the conductive layer 120.

A passivation layer 131 prevents the sensing target material 10 from leaking to the substrate 110 area. Therefore, the sensor 100 is prevented from operating in error due to the sensing target material 10 flowing to the circuit line 124. Also, the passivation layer 131 may have a certain height to prevent the sensing target material from moving. The passivation layer 131 may collect the sensing target material 10 in the sensing electrode 122.

The passivation layer 131 has a surface energy greater than that of the substrate 110 to allow the sensing target material 10 to form liquid crystals in the passivation layer 131, whereby the sensing target material 10 may not be diffused toward the substrate 110.

The passivation layer 131 may include a first opening 131a for exposing at least a portion of the sensing electrode 122. Only a partial area exposed through the first opening 131a may be used as the sensing electrode 122.

The sensing electrode 122 has a total length A of 400 µm to 5000 µm, and may be exposed at a length of 50 µm to 5000 µm through the first opening 131a. As the case may be, the total length of the sensing electrode 122 may be equal to the length of the sensing electrode 122 exposed through the first opening 131a, or the sensing electrode 122 may partially be exposed through the first opening 131a.

The length of the sensing electrode 122 exposed through the first opening 131a affects resolution of the sensor 100, printing reproducibility according to mass production and reliability of the sensor 100. The shorter the length of the sensing electrode 122 exposed through the first opening 131a is, the more improved resolution of the sensor 100 may be.

A width B of the sensing electrode 122 may be provided within the range of 50 μm to 1000 μm. The narrower the width B of the sensing electrode 122 is, the more improved resolution of the sensor 100 may be. However, a too narrow width of the sensing electrode 122 may cause an unstable printing process of the conductive layer 120. Preferably, the width B of the sensing electrode 122 is 50 μm to 200 μm for a stable printing process.

Supposing that both poles of the sensing electrode 122 are a first sensing electrode 122a and a second sensing electrode 122b, an interval C between the first sensing electrode 122a and the second electrode 122b may be provided within the range of 50 nm to 3000 μm.

However, if the interval C between the first sensing electrode 122a and the second electrode 122b is too wide and the amount of the sensing target material is not enough, it may be difficult to perform exact measurement. That is, the sensing target material should be in contact with the first sensing electrode 122a and the second sensing electrode 122b by forming a liquid drop. Considering this, the interval C between the first sensing electrode 122a and the second electrode 122b is preferably provided within the range of 900 μm to 1500 μm.

A height D of the sensing electrode 122 may be 700 nm to 15 μm. The height D of the sensing electrode 122 may affect a thickness of the sensor 100 and durability and reliability of the sensing electrode 122. If the height D of the sensing electrode 122 is lower than 70 nm, a problem may occur in that the sensing electrode 122 is lost in accordance with repetition of sensing. Due to a limitation of the printing process and to prevent the thickness of the sensor 100 from being increased, it is preferable that the height of the sensing electrode 122 is lower than 15 μm.

An antenna insulating layer 132 and an antenna bridge 140 form a structure for connecting the antenna pattern 121 with the circuit line 124. If the antenna pattern 121 is formed in a screw shape by being wound in the substrate 110, one end of the antenna pattern 121 should be extended toward a direction where the other end of the antenna pattern 121 is provided. The antenna bridge 140 forms this extended area, and the antenna insulating layer 132 may be provided between the antenna bridge 140 and the antenna pattern 121 such that the antenna bridge 140 is not interfered with the antenna pattern 121 printed through the existing printing process.

A protective layer 160 may be formed of an insulating material and arranged to face one surface of the substrate 110 so as to cover the substrate 110 and all of components packaged in the substrate 110, such as the conductive layer 120 and the passivation layer 131, thereby electrically and physically protecting the corresponding components. However, the protective layer 160 may include a second opening 160a for exposing the first opening 131a of the passivation layer 131.

A device 150 may be packaged in the substrate 110 and thus electrically connected with the circuit line 124.

Various electronic components related to operation of the sensor 100 may be implemented by the device 150. The electronic components, for example, may include a power generator, a controller, a converter, and a communication unit.

The radio signal received through the antenna pattern 121 is transferred to the device 150 through the circuit line 124. The device 150 may generate an alternating current power source through the direct current power source supplied thereto and input the generated alternating current power source to the sensing electrode 122.

Figure 3:
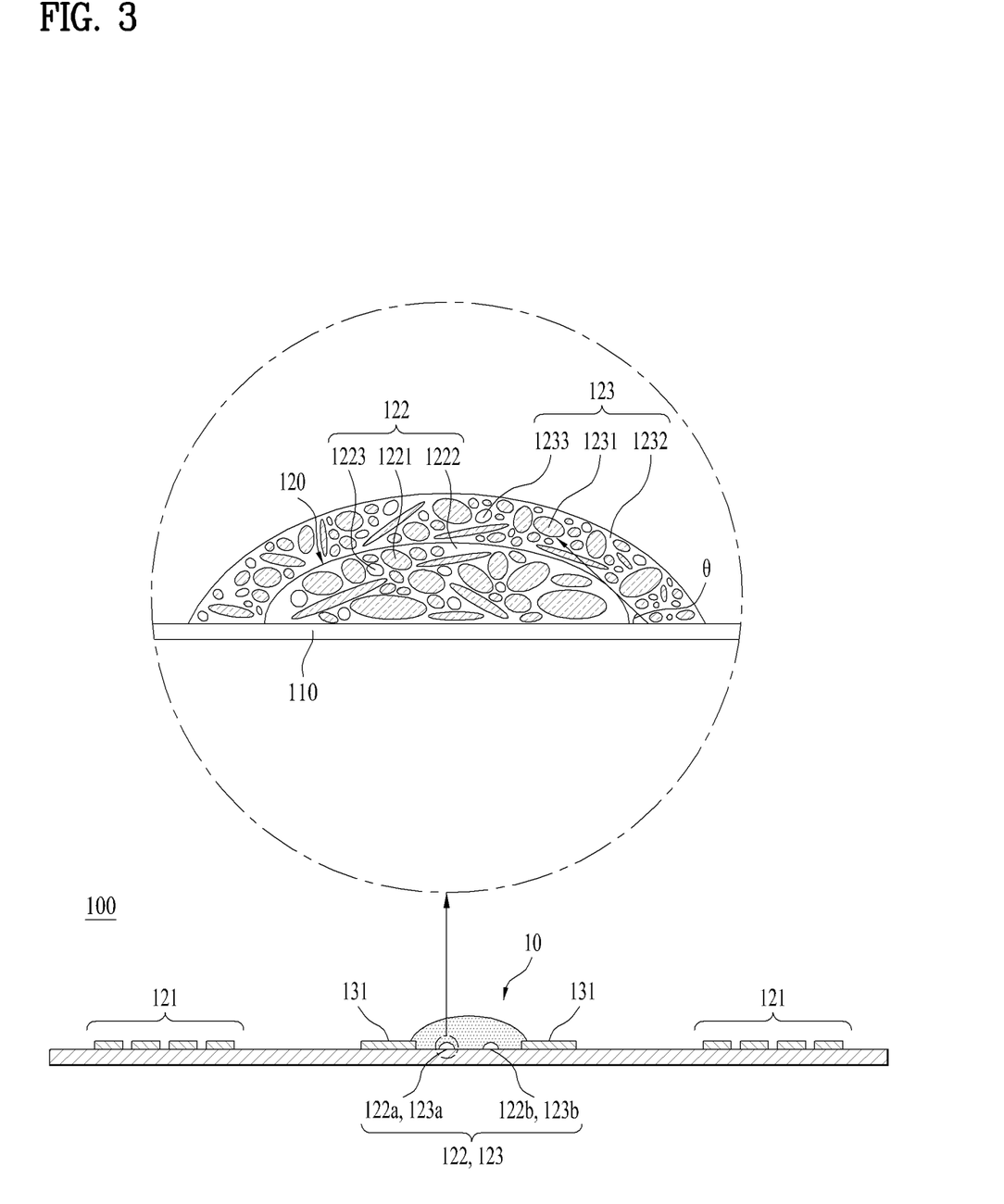
FIG. 3 is a cross-sectional view illustrating an area A-A' of FIG. 1.
Figure 4:
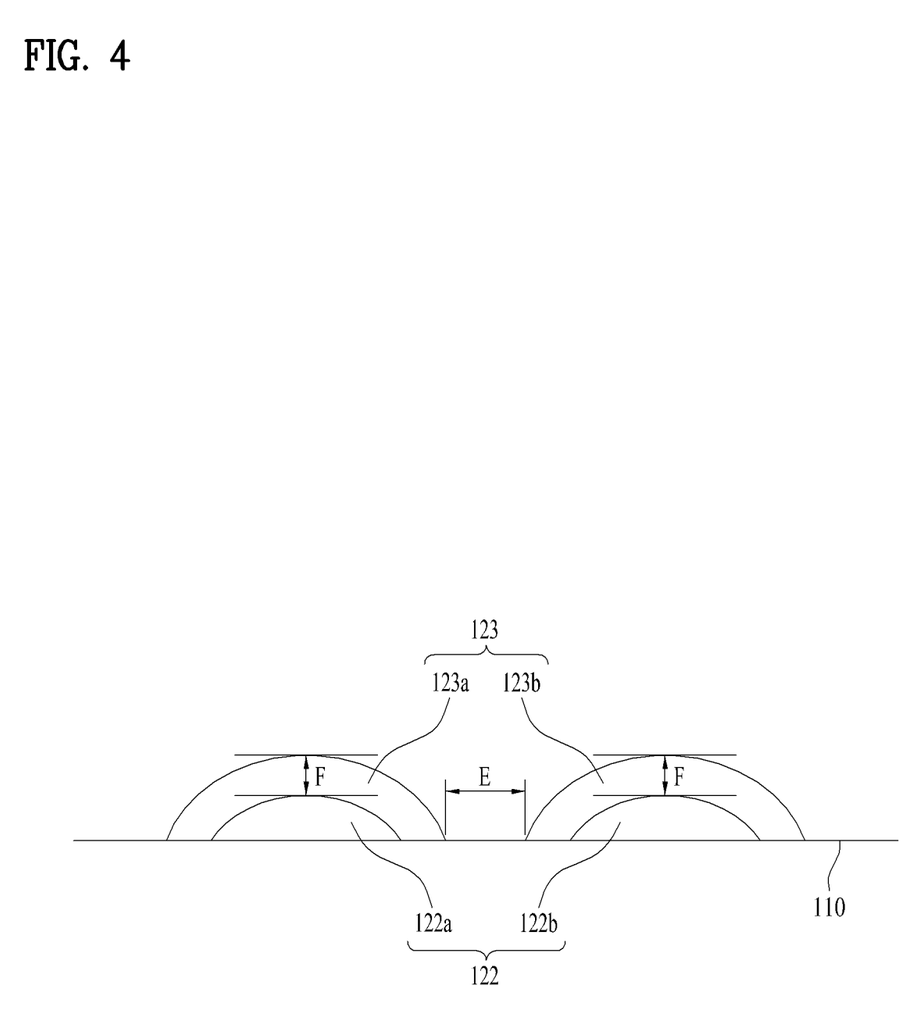
FIG. 4 is a partially enlarged view illustrating an area A-A' of FIG. 1.

FIG. 3 is a cross-sectional view illustrating an area A-A' of FIG. 1, and FIG. 4 is a partially enlarged view illustrating an area A-A' of FIG. 1. For convenience of description, description will be given with reference to FIGS. 3 and 4 together.

The sensing electrode 122 is direction in contact with the sensing target material 10, and if the sensing electrode 122 is formed by a vacuum deposition method, it is sufficient that the area of the sensing electrode 122 is only made of a material such as Pt or Au. However, as described above, if the antenna pattern and the circuit line are configured as the same layer through the electronic printing method, a material cost is too increased.

This problem may be solved by replacing the sensing electrode 122 with a material such as Ag, Cu and Al.

That is, Ag, Cu and Al may be provided as main components of the sensing electrode 122.

The sensing electrode 122 may be made of a combined component of conductive particles 1221 such as Ag, Cu and Al and a binder 1222 of an organic material. The conductive particles 1221 may have a spherical shape or a flake shape. The flake shaped conductive particles 1221 may have conductivity relatively higher than that of the spherical shaped conductive particles.

The conductive particles 1221 may have a size of several tens of nm to 20 μm to make sure of a reaction specific surface area. The sensing electrode 122 causes an impedance change by reaction with the sensing target material 10, and a capacitance component and a resistance component exist in the impedance. If the reaction specific surface area of the conductive particles 1221 is widened, oxidation or corrosion of the sensing electrode by reaction may be suppressed, and lifespan of the sensor 100 may be extended.

The binder 1222 supports the conductive particles 1221. The binder 1222 may serve to improve durability and reliability of the sensing electrode 122.

The binder 1222 may include at least one resin selected from a Polyethylene oxide (PEO) based group, an Oleic acid based group, an Acrylate based group, an Acetate based group and an Epoxy based group.

The sensing electrode 121 may have pores 1223. The pores 1223 may have a size of several nm to several tens of μm. If the sensing electrode 121 has pores 1223, since the sensor 100 is not damaged easily by repeated mechanical deformation, reliability of the sensor 100 may be improved.

The sensing electrode 122 may form an acute angle with the substrate 110. That is, a corner area of the sensing electrode 122 forms a slow inclination from the substrate 110 so that the sensing electrode 122 is not easily separated from by bending of the substrate 110.

However, if the sensing electrode 122 is exposed to be in contact with the sensing target material 10, a standard reduction potential of a material such as Ag, Cu and Al may be lowered, whereby it is likely that the sensing electrode 122 is corroded. Corrosion of the sensing electrode 122 disturbs a contact between the sensing target material 10 and the sensing electrode 122 and causes occurrence of noise in impedance measurement.

Also, a surface area of the sensing electrode 122 which is in contact with the sensing target material 10 is reduced due to sizes of the particles of the sensing electrode 122. This reduction of the contact surface area also acts to cause reduce exactness of sensing.

Three types of embodiments for improving conductivity and reliability and durability of conductive sensing due to the configuration of the sensing electrode 122 will be described later.

Embodiment 1

The coating electrode 123 may be provided outside the sensing electrode 122.

The coating electrode 123 may additionally be provided on an outer side of the sensing electrode 122 through the electronic printing method such that the sensing electrode 122 may be treated with sensitization.

The possibility of occurrence of noise in an impedance change sensed by the sensing electrode 122 is reduced due to the coating electrode 123. That is, the coating electrode 123 serves to increase electric conductivity of the sensing target material 10 and the sensing electrode 122.

Moreover, the coating electrode 123 may enhance durability and wear resistance of the sensing electrode 122.

The coating electrode 123 may be provided to be similar to the sensing electrode 122. That is, the coating electrode 123 may be provided by combination of conductive particles 1231 and a binder 1232.

The conductive particles 1231 of the coating electrode 123 may include a carbon nano tube (CNT).

The binder 1232 of the coating electrode 123 may minimize a gap 1233 by connecting the conductive particles 1231 of the coating electrode 123. The binder of the coating electrode 123 may include at least one resin selected from Polyethylene oxide (PEO) based group, Oleic acid based group, Acrylate based group, Acetate based group and Epoxy based group.

However, if the conductive particles 1231 of the coating electrode 123 are made of a carbon nano tube only, since resistance is high, sensing resolution is degraded. Therefore, the conductive particles 1231 of the coating electrode 123 may additionally include Graphite. Graphite serves to enhance conductivity of the sensing electrode 122.

Also, the conductive particles 1231 of the coating electrode 123 may include a carbon black. The carbon black serves to enhance durability or wear resistance of the sensing electrode 122.

The Graphite and the carbon black may be configured at 10% or more of a total mass of a conductive material.

The carbon nano tube, the graphite and the carbon black of the conductive particles 1231 perform the above functions by being organically associated with one another without performing each function independently.

The coating electrode 123 may be provided to cover the outer side of the sensing electrode 122. Pores 1223 of the sensing electrode 122 serve to have durability for mechanical deformation of the sensor 100 as described above. On the contrary, the pores 1223 disturbs exact impedance measurement by lowering conductivity of the sensing electrode 122. The coating electrode 123 allows the sensing electrode 122 filled with the pores 1223 to have high conductivity, whereby exact impedance can be measured.

As described above, the sensing electrode 122 has two electrodes 122a and 122b spaced apart from each other to be in contact with the sensing target material 10. This case is equally applied to the coating electrode 123.

The first coating electrode 123a and the second coating electrode 123b of the coating electrode 123 may be spaced apart from each other at an interval of 10 μm. This value corresponds to an approximate value, and the interval does not require 10 μm, exactly.

The thickness of the coating electrode, that is, the thickness from the uppermost end of the sensing electrode 122 to the uppermost end of the coating electrode 123 may be 10 μm or less.

The aforementioned passivation layer 131 may be provided outside the coating electrode 123. That is, the sensing electrode 122, the coating electrode 123 and the passivation layer 131 may sequentially be deposited at the outside from the substrate 110. Therefore, a length condition of the coating electrode 123 may be applied equally to the length condition of the sensing electrode 122. Therefore, the coating electrode 123 may be exposed to the outside through the first opening 131a as much as the length of the sensing electrode 122.

Embodiment 2

Unlike the aforementioned coating electrode, a conjugate polymer layer may be used to improve conductivity of the sensing electrode 122. The conjugate polymer layer may include a material such as a conductive polymer (PEDOT: PSS/P3HT). The conjugate polymer layer may be implemented in the sensing electrode 122 by a patterning process, or may be removed after being absorbed in the sensing electrode 122 for a certain time in a state that it is coated on a front surface.

Embodiment 3

To improve conductivity of the sensing electrode 122 and maintain measurement reliability, the sensing electrode 122 may be pressed through a rolling process. In a state that the sensing electrode 122 is printed, a certain temperature may be increased, and in a state that the increased temperature is maintained, the sensing electrode 122 may be pressed through a roller.

However, if the sensing electrode 122 is pressed through the rolling process, coupling of the sensing electrode 122 may be broken by pressure. To minimize this phenomenon, a groove may be formed in the roller and then the rolling process may be performed.

Figure 5:
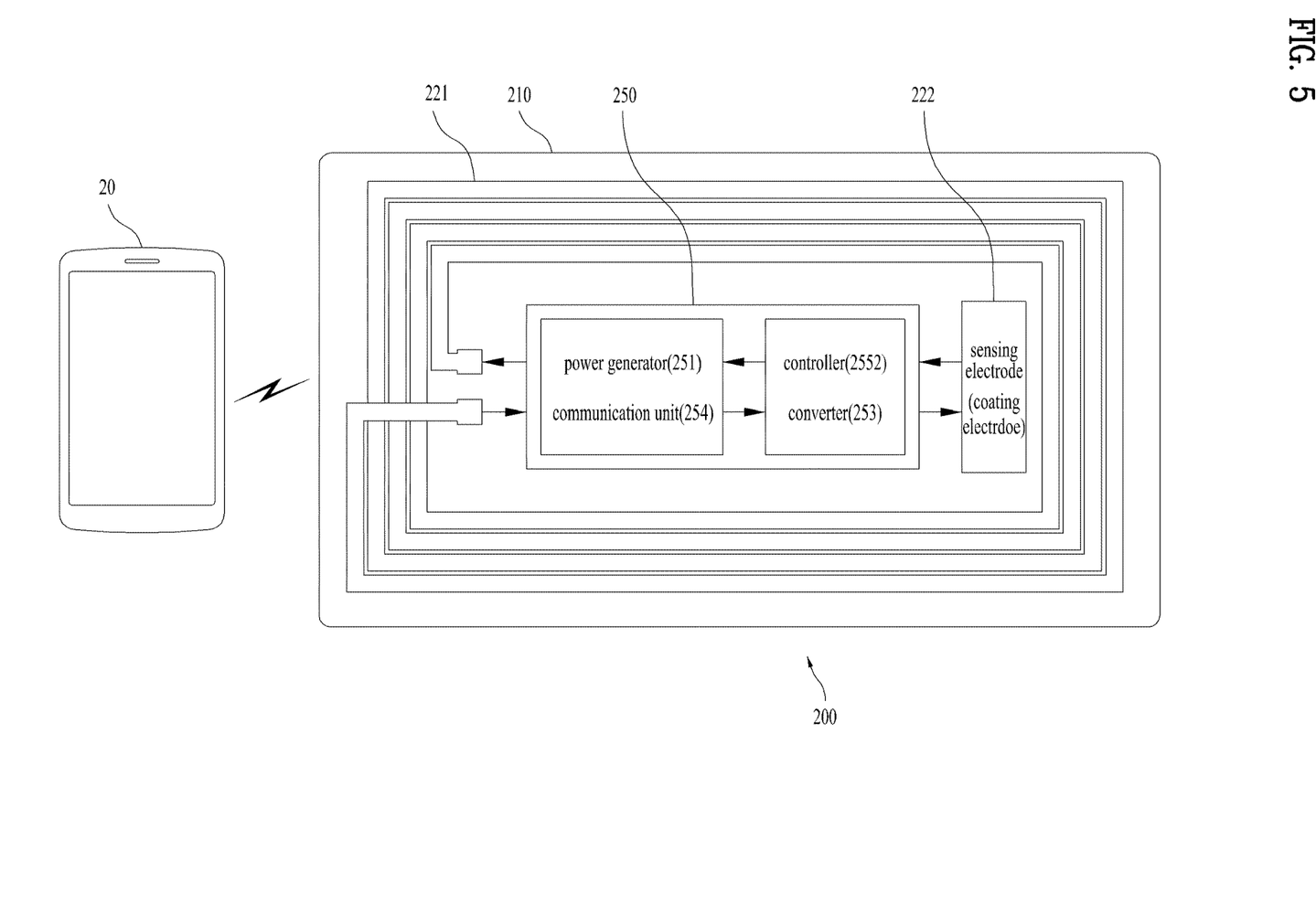
FIG. 5 is a view illustrating a sensor of the present invention, which is linked to an external device.

FIG. 5 is a view illustrating a sensor 200 of the present invention, which is linked to an external device 20.

Hereinafter, a description will be given based on the sensor type of the embodiment 1 unless mentioned separately. However, the description may equally be applied to the embodiments 2 and 3 within the range that does not depart from contradiction.

A description will be given based on that the external device 20 is a mobile terminal, especially smartphone although the external device 20 may have various types.

The sensor 200 transmits or receives a radio signal to or from an external device through an antenna pattern 221.

The sensor 200 generates a direct current power source through a power generator 251 to drive a circuit unit 250. In this way, the sensor 200 of the present invention does not have a component for power supply but generates a direct current power source by using the radio signal received from the external device 20. A controller 252, a converter 253, a communication unit 254 and a sensing electrode 222 are operated by the generated direct current power source.

The controller 252 is driven by the direct current power source which is supplied. The controller 252 generates an alternating current voltage and inputs the generated alternating current voltage to the sensing electrode 222. Based on the case of the embodiment 1, the sensing electrode 222 may refer to a concept that includes a coating electrode 123 (see FIG. 3). The sensing electrode 222 which will be described later may include a coating electrode.

If the sensing electrode 222 is reacted with a sensing target material, the sensing electrode 222 causes an impedance change. The impedance change of the sensing electrode 222 is represented by a change of the alternating current voltage generated by the controller 252. The sensing target material may be identified in accordance with a range of an output value.

The change of the alternating current voltage may be changed to a digital signal. The converter 252 converts the change of the alternating current voltage represented based on the impedance change of the sensing electrode 222 to a digital signal. The communication unit 254 transmits the digitalized signal to the external device 20 through the antenna pattern. In this case, the communication unit 254 may be NFC Tag IC.

The external device 20 generates information by receiving the digitalized signal from the sensor 200 and stores and manages the generated information.

The external device 20 may display information through a display.

Figure 6:
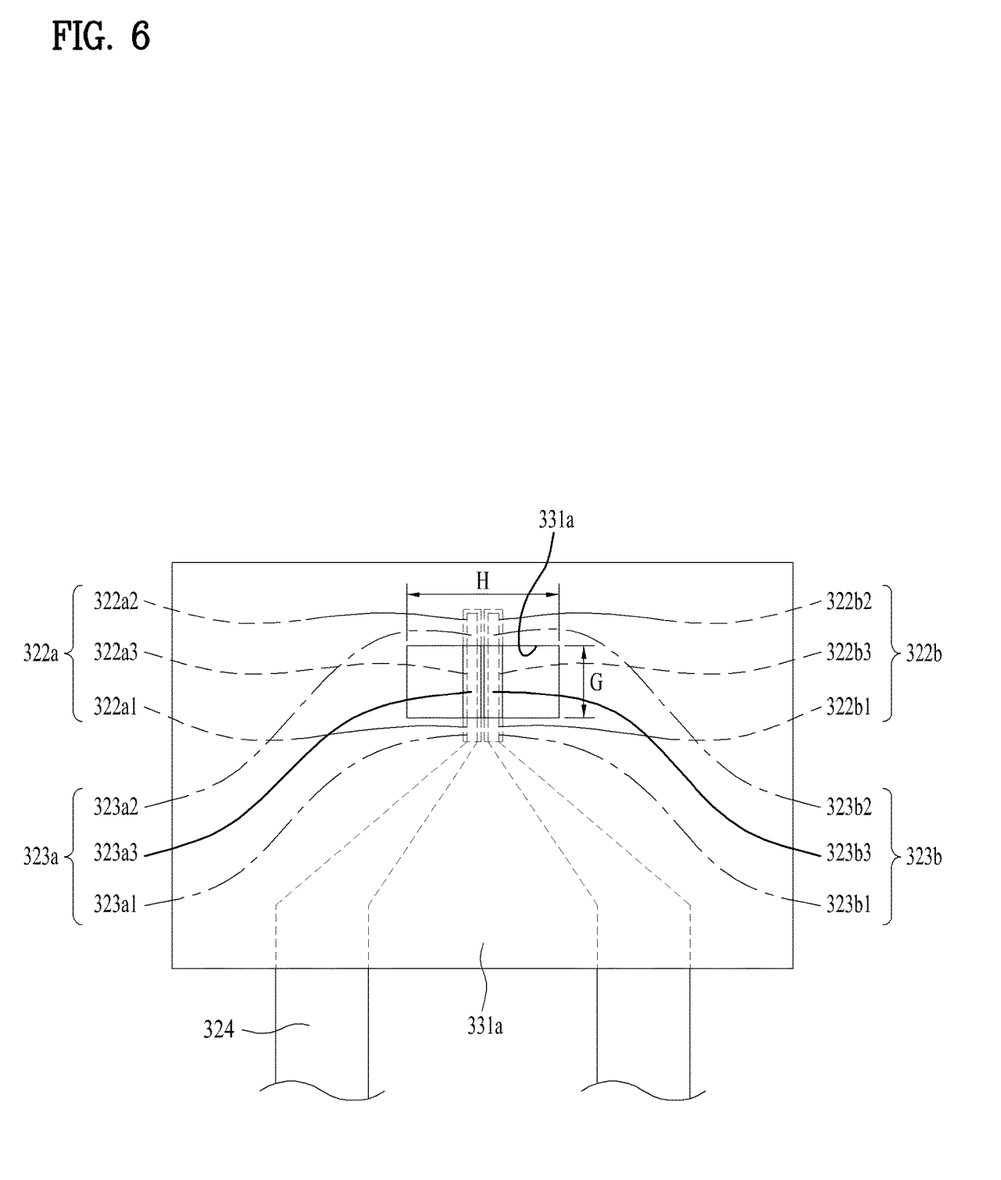
FIG. 6 is a conceptual view illustrating a structure of a circuit line, a sensing electrode, a coating electrode and a passivation layer.

FIG. 6 is a conceptual view illustrating a structure of a circuit line 324, a sensing electrode 322, a coating electrode 323 and a passivation layer 331.

The sensor is formed by printing, heat drying and hardening processes.

Particularly, if the printing process is repeated, a process error, especially alignment error may occur, and an error may occur due to contradiction of the substrate even during the heat drying process.

Resolution of the sensor may be determined in accordance with an exposed length of first and second sensing electrodes 322a and 322b. A total length and the exposed length of the first and second sensing electrodes 322a and 322b are 5,000 μm or less which is very short, whereby the process error is likely to be generated. Therefore, a structure for minimizing the process error is required.

The first sensing electrode 322a, the second electrode 322b, the first coating electrode 323a, the second coating electrode 323b, the circuit line 324 and the passivation layer 331 may be formed by the printing process. The passivation layer 331 is arranged to cover the first sensing electrode 322a, the second sensing electrode 322b, the first coating electrode 323a, the second coating electrode 323b and the circuit line 324. Therefore, the passivation layer 331 is formed after printing of the sensing electrodes 322a and 322b, the coating electrodes 323a and 323b and the circuit line 324. Therefore, the process error may occur due to repetition of the printing process and during the heat drying process. For this reason, the sensing electrodes 322a and 322b or the coating electrodes 323a and 323b may be exposed or covered unlike a design intention.

The sensing electrodes 322a and 322b and the coating electrodes 323a and 323b may be partitioned into three parts along a longitudinal direction. These three parts are defined as first end portions 322a1, 322b1, 323a1 and 323b1, second end portions 322a2, 322b2, 323a2 and 323b2, and center portions 322a3, 322b3, 323a3 and 323b3. The passivation layer 331 covers the first end portions 322a1, 322b1, 323a1 and 323b1 and the second end portions 322a2, 322b2, 323a2 and 323b2, and the first opening 331a exposes the center portions 322a3, 322b3, 323a3 and 323b3.

The sensing electrode 322 and the coating electrode 323 are formed to be longer than the length of the first opening 331a. The first opening 331a may control the exposed length of the sensing electrode 322 and the coating electrode 323. Therefore, a length G of the first opening 331a of the passivation layer 331 may be controlled accurately to lower an error.

It is preferable that a width H of the first opening 331a is wider than an interval between the first electrodes 322a and 323a and the second electrodes 322b and 323b of the sensing electrode 322 or the coating electrode 323 and does not exceed 5000 μm. If the width H of the first opening 331a is too wide, a sensing target material, which will be in contact with the sensing electrode 322 or the coating electrode 323, may be diffused without forming a liquid drop.

Referring to an experimental result, the shorter the length of the sensing electrode 322 or the coating electrode 323 exposed through the first opening 331 is, the narrower the width of the sensing electrode 322 or the coating electrode 323 is, and the wider the interval between the two electrodes is, the more improved resolution is. However, if the sensing electrode 322 and the coating electrode 323 are designed only for the purpose of improving resolution, a problem of durability and reliability may occur. Therefore, considering resolution, durability and reliability, the structure of the sensing electrode 322 and the coating electrode 323 should be designed.

Figure 7:
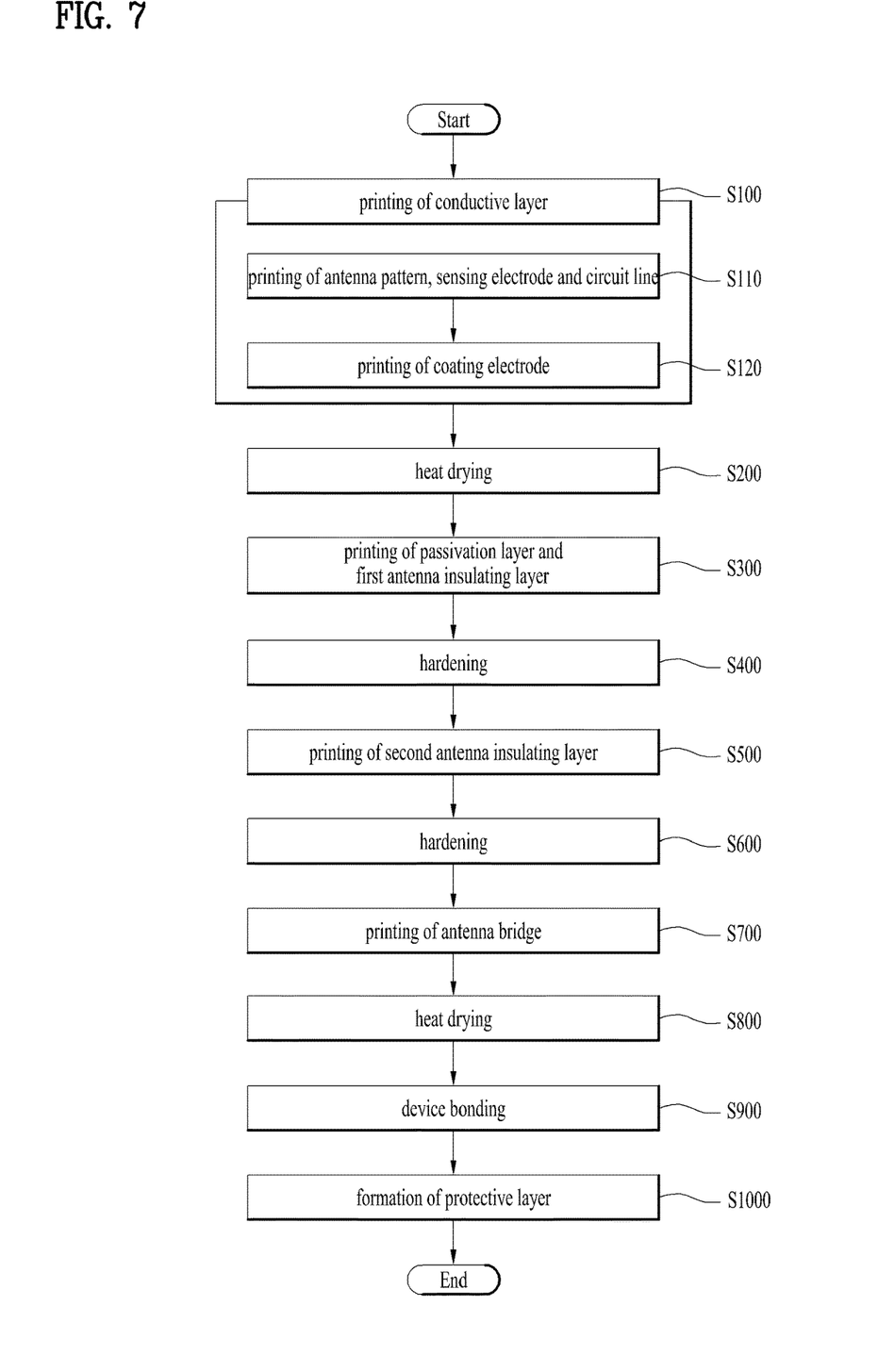
FIG. 7 is a flow chart illustrating a manufacturing method for a sensor related to the present invention.
Figure 8:
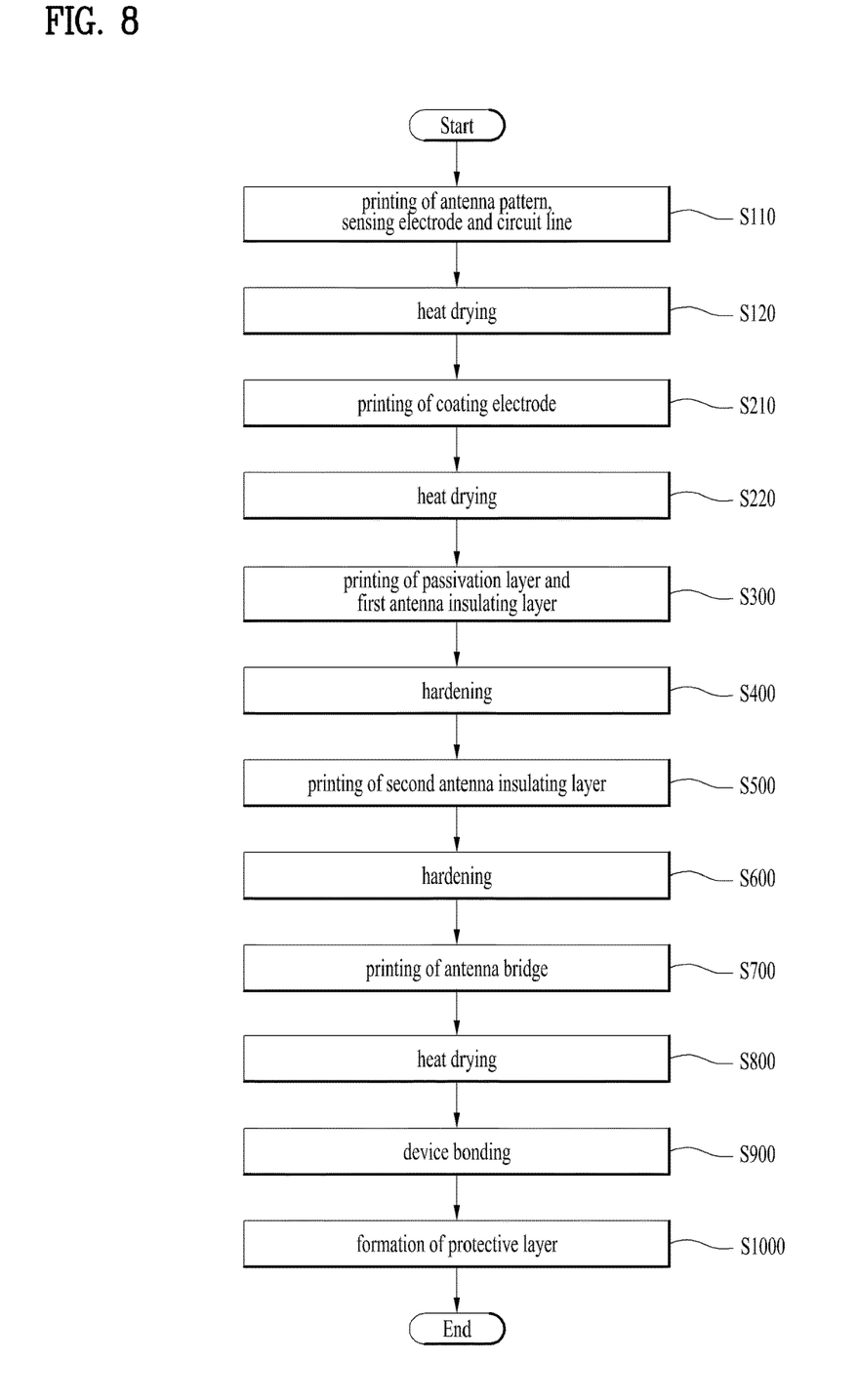
FIG. 8 is a flow chart illustrating another method for a sensor related to the present invention.

FIGS. 7 and 8 are flow charts illustrating a manufacturing method for a sensor related to the present invention.

Referring to FIG. 7, the conductive layer is printed on the substrate through the printing process (S100). The conductive layer includes an antenna pattern, a sensing electrode, a coating electrode and a circuit line.

If the antenna pattern, the sensing electrode and the circuit line are made of the same material, the antenna pattern, the sensing electrode and the circuit line of the conductive layer may be formed simultaneously by a printing process of one time (S110). Therefore, this may reduce material and manufacturing costs. This will be defined as a first printing process for convenience. The antenna pattern, the sensing electrode and the circuit line may be provided on the same layer due to the first printing process.

Afterwards, the coating electrode may be printed on the outer side of the sensing electrode (S120). Since the coating electrode is made of a material different from that of the sensing electrode, the coating electrode may be formed through additional second printing process.

Therefore, the coating electrode configures a hetero-layer deposited on a layer provided with the sensing electrode.

The printing process of the conductive layer uses a powdered ink or paste. A composition of the powdered ink or paste may include conductive particles of 40 weight % to 70 weight %, and an organic material of 30 weight % to 60 weight % containing solvent. As a result, oxidation and corrosion of the sensing electrode or the coating electrode may be minimized.

As described above, the conductive particles of the sensing electrode may be made of at least one of Ag, CU and Al. Meanwhile, the conductive particles of the coating electrode may be made of at least one of carbon nano tube, graphite and carbon black.

The conductive particles of the sensing electrode or the conductive particles of the coating electrode may have a spherical shape or a flake shape.

A solvent for mixing the conductive particles with the binder may include at least one selected from a group of Acetone, Allyl alcohol, Acetic acid, Acetol, Methyalcohol and Benzene.

The printing process of the conductive layer 120 may be any one of Screen, offset, and Gravure.

After the printing process, the conductive layer may be hardened through heat drying (S200). Heat drying may be performed at 80° C. to 200° C. The aforementioned solvent may be evaporated during heat drying. To enable the process of a low temperature of 200° C. or less, it is preferable that the conductive particles have a size of several tens of nm to 20 μm in the form of powder.

Particularly, heat drying may be performed after a first printing process for printing the sensing electrode and a second printing process for printing the coating electrode. As the coating electrode is printed on the sensing electrode prior to heat drying, the coating electrode enters a portion between gaps of the sensing electrode, whereby the sensing electrode and the coating electrode may be coupled to each other more densely. If the sensing electrode and the coating electrode are coupled to each other densely, conductivity is enhanced, and the coating electrode may be prevented from being easily separated from the substrate or the sensing electrode by a high coupling force.

Alternatively, as shown in FIG. 8, after the first printing process of the sensing electrode, the heat drying process may be performed primarily and then the second printing process may be performed for the coating electrode.

After the heat drying process is completed for both the first printing process and the second printing process, the passivation layer and the antenna insulating layer may be printed (S300).

The passivation layer and the antenna insulating layer may be made of the same material, and therefore may be formed at the same time through one printing process. That is, the passivation layer and the antenna insulating layer may form the same layer on the conductive layer.

The printed passivation layer and antenna insulating layer may be hardened (S400). The passivation layer and the antenna insulating layer may be hardened by ultraviolet (UV) rays.

The printing processes may be performed multiple times to make sure of sure insulation reliability (S500). At this time, the antenna insulating layer which is first printed may be defined as a first antenna insulating layer, and the antenna insulating layer which is printed later may be defined as a second antenna insulating layer. After the second antenna insulating layer is printed, the second antenna insulating layer may be further hardened in the same manner as the hardening process of the first antenna insulating layer (S600).

If necessary, in addition to the first antenna insulating layer and the second antenna insulating layer, additional antenna insulating layer may be printed. In this case, the same hardening process as that of the first antenna insulating layer or the second antenna insulating layer is performed.

An antenna bridge is printed on the antenna insulating layer (S700). The antenna bridge may be made of the same material as that of the conductive layer.

The antenna bridge may be heat-dried in the same manner as the conductive layer (S800). Details of a heat drying condition are the same as those described in the heat drying process of the conductive layer.

Next, the device may be bonded to the substrate (S900). The device is electrically connected with the circuit line.

Afterwards, the protective layer may be covered on the substrate to protect the components packaged in the substrate (S1000).

Figure 9:
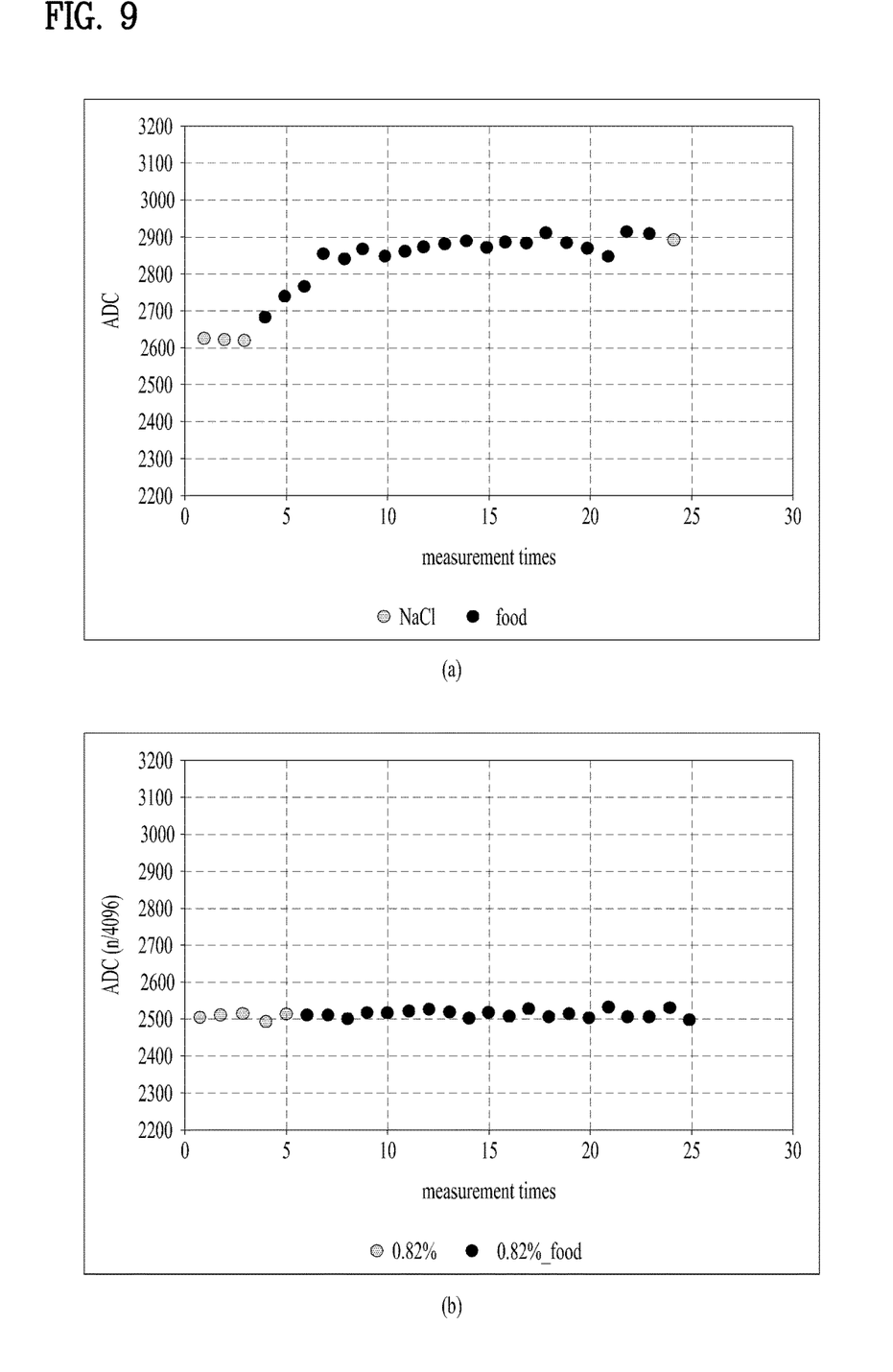

FIGS. 9(a) and 9(b) are graphs illustrating that ADC change according to measurement times for each of a sensor of the related art and a sensor of the present invention is measured.

As shown, it is noted that an ADC value according to measurement times is uniformly maintained without change when Nacl and food are sequentially measured through the sensor of the present invention unlike the sensor of the related art. Therefore, it is noted that a resultant value of high reliability can be obtained by the user of the sensor without the problem of corrosion or durability.

MODE FOR CARRYING OUT THE INVENTION

It will be apparent to those skilled in the art that the present specification can be embodied in other specific forms without departing from the spirit and essential characteristics of the specification.

The above embodiments are therefore to be construed in all aspects as illustrative and not restrictive. The scope of the specification should be determined by reasonable interpretation of the appended claims and all change which comes within the equivalent scope of the specification are included in the scope of the specification.

INDUSTRIAL APPLICABILITY

As described above, the present invention is fully or partially applicable to all sensors.

The invention claimed is:

1. A sensor comprising:
a non-conductive substrate; and
a conductive layer electronically printed on one surface of the substrate,
wherein the conductive layer includes:
an antenna pattern for transmitting or receiving a radio signal to or from an external device;
a sensing electrode connected to the antenna pattern through a circuit line, for sensing an impedance change due to a contact with a sensing target material; and
a coating electrode deposited on the sensing electrode, for removing an occurrence of noise of the impedance change, and
wherein each of the sensing electrode and the coating electrode includes:
a plurality of conductive particles forming a gap; and
a binder having the plurality of conductive particles to fill the gap.

2. The sensor of claim 1, wherein the conductive particles of the sensing electrode include Ag.

3. The sensor of claim 1, wherein the conductive particles of the coating electrode include a carbon nano tube (CNT).

4. The sensor of claim 3, wherein the conductive particles of the coating electrode further include a Graphite and a carbon black.

5. The sensor of claim 4, wherein the graphite and the carbon black are configured at 10% or less of a total mass of the coating electrode.

6. The sensor of claim 1, wherein the binder includes one of a Polyethylene oxide (PEO) based resin, an Oleic acid based resin, an Acrylate based resin, an Acetate based resin and an Epoxy based resin.

7. The sensor of claim 1, wherein the conductive particles are configured by combination of a flake or spherical shape.

8. The sensor of claim 1, wherein the antenna pattern, the circuit line and the sensing electrode are made of the same material, provided on the same layer, and the coating electrode is provided by being deposited on the sensing electrode.

9. The sensor of claim 1, wherein the sensing electrode includes two electrodes spaced apart from each other, the coating electrode includes a first area and a second area, which respectively cover the spaced electrodes, and a minimum distance between the first area and the second area is 10 μm, and a thickness of the coating electrode from an upper end of the sensing electrode is 10 μm.

10. The sensor of claim 1, wherein the sensing electrode includes two electrodes spaced apart from each other, and an interval between the two electrodes is 30 μm or more and 3000 μm or less.

11. The sensor of claim 9, wherein the antenna pattern, the sensing electrode and the circuit line have a thickness of 0.5 μm or more and 15 μm or less.

12. The sensor of claim 1, wherein the substrate includes any one of polyethylene erephthalate (PET), polyimide (PI), polystyrene (PS) and polyethylene naphthalate (PEN).

13. The sensor of claim 1, wherein the antenna pattern has a width of 500 μm or more and 1500 μm or less, and an adjacent distance of the antenna pattern is 300 μm or more and 700 μm or less.

14. The sensor of claim 1, further comprising a passivation layer forming an opening, which exposes at least one area of the sensing electrode, having a surface energy greater than that of the substrate.

15. The sensor of claim 14, further comprising a protective layer deposited on the substrate, protecting the conductive layer and the passivation layer.

16. The sensor of claim 1, wherein the conductive layer includes a conjugate polymer layer containing a conductive polymer provided by being patterned or absorbed in the sensing electrode.

17. The sensor of claim 1, wherein the sensing electrode is pressed through a rolling process.

18. A manufacturing method of a sensor, comprising:
a first printing step of printing, on a non-conductive substrate, a sensing electrode connected with an antenna pattern through a circuit line for transmitting or receiving a radio signal to or from an external device and sensing an impedance change due to a contact of a sensing target material;
a second printing step of printing a coating electrode on an outer side of the sensing electrode, for removing occurrence of a noise of the impedance change; and
a drying step of heat drying the printed antenna pattern, sensing electrode and coating electrode,
wherein each of the sensing electrode and the coating electrode includes:
a plurality of conductive particles forming a gap; and
a binder having the plurality of conductive particles to fill the gap.

19. The manufacturing method of claim 18, wherein the first printing step and the second printing step are performed by any one of a Gravure offset process, a Gravure printing process and a Screen printing process.

* * * * *